US012661530B2

(12) United States Patent
Tsutsui

(10) Patent No.: US 12,661,530 B2
(45) Date of Patent: Jun. 23, 2026

(54) PARTICLE BEAM THERAPY DEVICE

(71) Applicant: SUMITOMO HEAVY INDUSTRIES, LTD., Tokyo (JP)

(72) Inventor: Hiroshi Tsutsui, Tokyo (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 241 days.

(21) Appl. No.: 18/465,699

(22) Filed: Sep. 12, 2023

(65) Prior Publication Data

US 2023/0414970 A1      Dec. 28, 2023

Related U.S. Application Data

(63) Continuation of application No. PCT/JP2022/011023, filed on Mar. 11, 2022.

(30) Foreign Application Priority Data

Mar. 19, 2021      (JP) .................................. 2021-045657

(51) Int. Cl.
 *A61N 5/10*          (2006.01)
 *G21K 1/093*         (2006.01)
        (Continued)

(52) U.S. Cl.
 CPC ......... *A61N 5/1081* (2013.01); *A61N 5/1078* (2013.01); *G21K 1/093* (2013.01);
        (Continued)

(58) Field of Classification Search
 CPC ................ A61N 5/1081; A61N 5/1078; A61N 2005/1087; A61N 2005/1095;
        (Continued)

(56) References Cited

U.S. PATENT DOCUMENTS 3,617,705 A * 11/1971 Takano ................ G01N 23/207
                                                  378/72
4,112,306 A *  9/1978 Nunan ..................... A61N 5/10
                                                  976/DIG. 428
        (Continued)

FOREIGN PATENT DOCUMENTS

CN          102695544 A      9/2012
EP          2 602 003 A1      6/2013
        (Continued)

OTHER PUBLICATIONS

International Search Report of PCT/JP2022/011023, mailed on May 31, 2022.
        (Continued)

*Primary Examiner* — David A Vanore
(74) *Attorney, Agent, or Firm* — WTA IP Law P.C.

(57)                    ABSTRACT

A particle beam therapy device that irradiates a patient with a cation beam to perform treatment, the device including a passage selection unit that selectively passes through the cation beam among a mixed beam in which the cation beam and other species of a beam having a nuclide different from that of the cation beam are mixed after passing through a deflection magnetic field, after causing the mixed beam to pass through the deflection magnetic field, in a case where the other species of the beam is generated from the cation beam.

13 Claims, 6 Drawing Sheets

(51) Int. Cl.
    *H05H 7/04*        (2006.01)
    *H05H 7/10*        (2006.01)
    *H05H 13/00*     (2006.01)

(52) U.S. Cl.
    CPC ................ *H05H 7/04* (2013.01); *H05H 7/10*
        (2013.01); *H05H 13/005* (2013.01); *A61N*
        *2005/1087* (2013.01); *H05H 2007/045*
        (2013.01); *H05H 2277/11* (2013.01)

(58) Field of Classification Search
    CPC ............... A61N 5/1077; A61N 5/1045; A61N
        2005/1085; G21K 1/093; G21K 1/02;
        G21K 5/04; H05H 7/04; H05H 7/10;
        H05H 13/005; H05H 2007/045; H05H
        2277/11
    See application file for complete search history.

(56) References Cited

U.S. PATENT DOCUMENTS

| | | | | |
|---|---|---|---|---|
| 4,204,119 | A | * | 5/1980 | Yasuno ..................... G01T 1/11 |
| | | | | 250/337 |
| 5,189,687 | A | * | 2/1993 | Bova .................... A61N 5/1031 |
| | | | | 378/68 |
| 6,683,318 | B1 | * | 1/2004 | Haberer ............... A61N 5/1081 |
| | | | | 250/492.3 |
| 9,630,027 | B2 | * | 4/2017 | Hanakawa ............... H05H 7/04 |
| 9,737,733 | B2 | * | 8/2017 | Lee .......................... G21K 1/08 |
| 11,348,755 | B2 | * | 5/2022 | Star-Lack ................ H05G 2/00 |
| 2006/0163496 | A1 | * | 7/2006 | Hiramoto ................. G21K 5/04 |
| | | | | 250/492.3 |
| 2007/0114464 | A1 | * | 5/2007 | Birgy ................... A61N 5/1079 |
| | | | | 250/494.1 |
| 2007/0131876 | A1 | * | 6/2007 | Brahme ............... A61B 6/4429 |
| | | | | 250/492.1 |
| 2008/0067451 | A1 | * | 3/2008 | Guertin ................ A61N 5/1081 |
| | | | | 250/503.1 |
| 2008/0290299 | A1 | * | 11/2008 | Hansmann ............... H05H 7/12 |
| | | | | 315/502 |
| 2009/0050819 | A1 | | 2/2009 | Ma et al. |
| 2011/0186746 | A1 | * | 8/2011 | Drees ................... A61N 5/1043 |
| | | | | 250/397 |
| 2012/0280150 | A1 | | 11/2012 | Jongen |
| 2015/0115179 | A1 | * | 4/2015 | Hiramoto ............ A61N 5/1048 |
| | | | | 250/492.3 |
| 2016/0199671 | A1 | | 7/2016 | Jongen |
| 2016/0287908 | A1 | * | 10/2016 | Bennett ................ A61N 5/1044 |
| 2017/0043187 | A1 | * | 2/2017 | Lee ...................... A61N 5/1044 |
| 2017/0128029 | A1 | * | 5/2017 | Penfold ................. A61B 6/4258 |
| 2018/0012727 | A1 | * | 1/2018 | Amato ................. A61B 6/4035 |
| 2018/0068753 | A1 | * | 3/2018 | Kamiguchi .......... A61N 5/1077 |
| 2018/0161601 | A1 | * | 6/2018 | Spotts ...................... G21K 5/04 |
| 2018/0369612 | A1 | * | 12/2018 | Gerbershagen ...... A61N 5/1081 |
| 2019/0030373 | A1 | * | 1/2019 | Miyashita ............ A61N 5/1081 |
| 2019/0151677 | A1 | | 5/2019 | Jongen |
| 2019/0351257 | A1 | | 11/2019 | Chen et al. |
| 2021/0299480 | A1 | * | 9/2021 | Sasai .................... A61N 5/1081 |
| 2022/0355129 | A1 | * | 11/2022 | Fujii .................... A61N 5/1068 |
| 2022/0379138 | A1 | * | 12/2022 | Miyoshi ................. G16H 30/40 |

FOREIGN PATENT DOCUMENTS

| | | |
|---|---|---|
| JP | 2008-525968 A | 7/2008 |
| JP | 2012-2772 A | 1/2012 |
| JP | 2019-107560 A | 7/2019 |
| JP | 2020-509919 A | 4/2020 |
| KR | 10-2015-0129959 A | 11/2015 |

OTHER PUBLICATIONS

Office Action of JP Application No. 2023-507063 Mailed on Sep. 2, 2025.

Office Action of the corresponding CN Application No. 202280021818.4 Mailed on Apr. 30, 2026.

* cited by examiner

MOMENTUM PER UNIT CHARGE

MOMENTUM PER UNIT CHARGE

PARTICLE BEAM THERAPY DEVICE

CROSS-REFERENCE TO RELATED APPLICATIONS

This is a bypass continuation of International PCT Application No. PCT/JP2022/011023, filed on Mar. 11, 2022, which claims priority to Japanese Patent Application No. 2021-045657, filed on Mar. 19, 2021, which are incorporated by reference herein in their entirety.

BACKGROUND

Technical Field

Certain embodiments of the present invention relate to a particle beam therapy device.

Description of Related Art

In the related art, as a technique in such a field, a proton beam therapy device described in the related art is known. In this type of proton beam therapy device, for example, the spread of the energy of the proton beam is cut by an energy selection system (ESS) combining a bending electromagnet, a quadrupole electromagnet, or the like.

SUMMARY

According to an embodiment of the present invention, there is provided a particle beam therapy device that irradiates a patient with a cation beam to perform treatment, in which the cation beam among a mixed beam in which the cation beam and other species of a beam having a nuclide different from that of the cation beam are mixed is selectively passed through a predetermined passage selection unit, after causing the mixed beam to pass through the deflection magnetic field, in a case where the other species of the beam is generated from the cation beam.

According to another embodiment of the present invention, there is provided a particle beam therapy device that irradiates a patient with a cation beam to perform treatment, the device including a cyclotron that exits the cation beam, a degrader that is provided on a downstream side of the cyclotron, reduces energy of the cation beam, and generates other species of a beam having a nuclide different from that of the cation beam from the cation beam when the energy is reduced, a bending electromagnet that is provided on a downstream side of the degrader, deflects a mixed beam in which the cation beam and the other species of the beam are mixed, and causes a trajectory of a beam included in the mixed beam to be different depending on momentum per unit charge, and a passage selection unit that is provided on a downstream side of the bending electromagnet, passes through the beam included in the mixed beam at a position of a trajectory of the cation beam in the mixed beam, and shields the beam included in the mixed beam at a position other than the position of the trajectory of the cation beam in the mixed beam.

DETAILED DESCRIPTION

Figure 1:
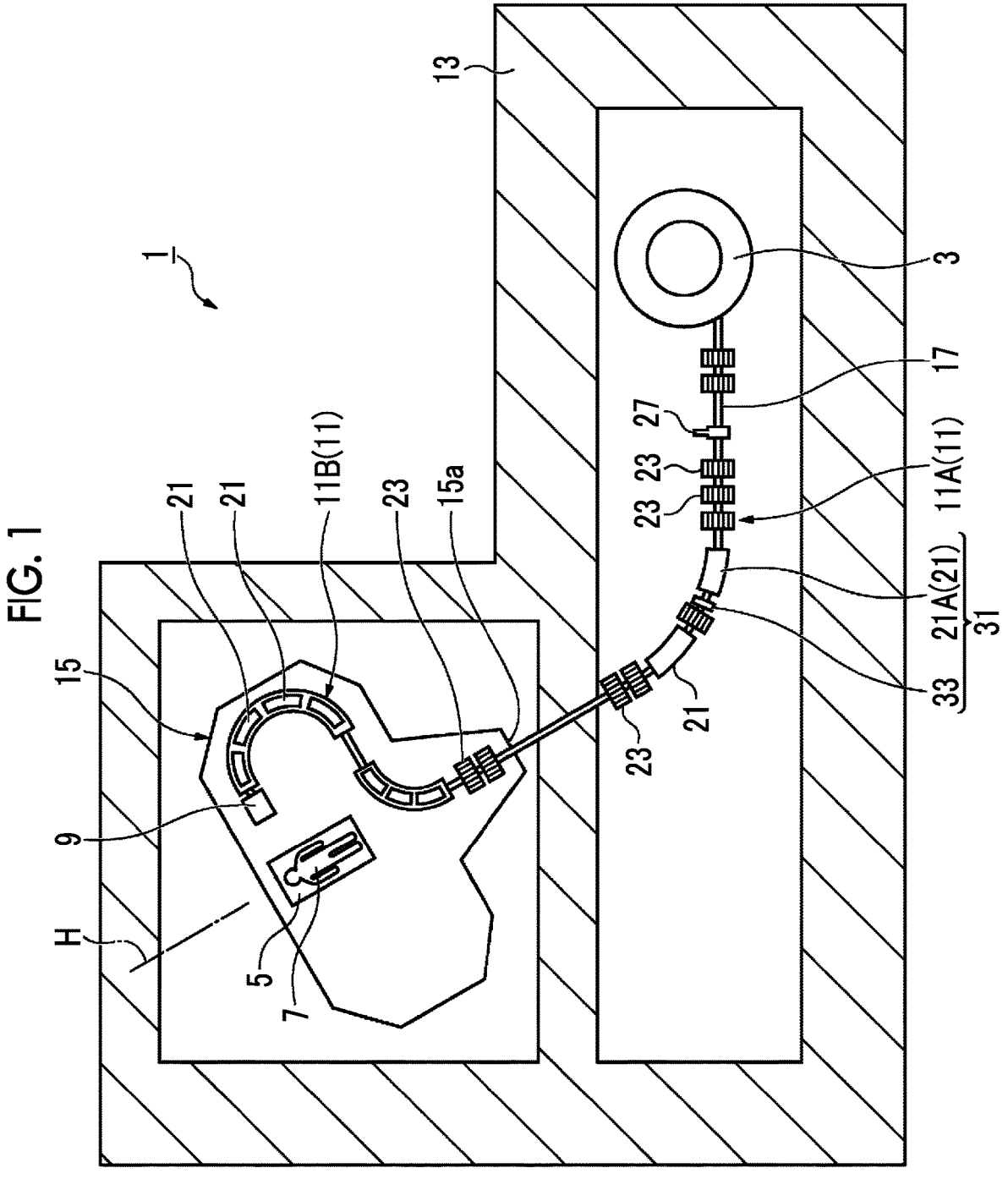
FIG. 1 is a disposition view in a plan view of a particle beam therapy device according to one embodiment of the present embodiment.

In the particle beam therapy device, another nuclide of a beam may be generated from the transport particle beam for treatment, and other species of a beam may be mixed with the particle beam for treatment. When the other species of the beam generated in this manner is irradiated to the patient to be treated, the other species of the beam reaches a portion deeper inside the patient body than the treatment beam because the mass number of the particles is small. In some cases, there is a risk of causing unnecessary damage to the portion. It is desirable to provide a particle beam therapy device that reduces an unnecessary particle beam irradiated to a patient.

According to this particle beam therapy device, since the cation beam of the mixed beam selectively passes through the passage selection unit, after the mixed beam passes through the deflection magnetic field, the other species of the beam is reduced in the beams transmitted to the downstream side of the passage selection unit.

The passage selection unit may pass through a beam having the same momentum per unit charge as momentum per unit charge of the cation beam in the mixed beam passed through the deflection magnetic field, and shield a beam having momentum per unit charge different from the momentum per unit charge of the cation beam in the mixed beam.

In this case, in the passage selection unit, since the cation beam included in the mixed beam and the other species of the beam having the same momentum per unit charge as that of the cation beam pass through, and the other species of the beam other than the above is shielded, the other species of the beam is reduced in the beams transmitted to the downstream side of the passage selection unit.

The deflection magnetic field may cause a trajectory of a beam included in the mixed beam to be different depending on the momentum per unit charge on an upstream side of the passage selection unit, and the passage selection unit may cause the beam included in the mixed beam to pass through at a position of a trajectory corresponding to the momentum per unit charge of the cation beam included in the mixed beam, and shield the beam included in the mixed beam at a position other than the position of the trajectory corresponding to the momentum per unit charge of the cation beam included in the mixed beam.

In this case, the trajectory of each of the beams included in the mixed beam is different depending on the momentum per unit charge by passing through the deflection magnetic field. In the passage selection unit, since the cation beam and the other species of the beam having the same momentum per unit charge as that of the cation beam pass through, and the other species of the beam other than the above is shielded, the other species of the beam is reduced in the beams transmitted to the downstream side of the passage selection unit.

The cation beam may be a helium ion beam, and the other species of the beam may include a deuterium ion beam. As a result, a helium beam therapy device is obtained in which the other species of the beam with which the patient is irradiated is reduced.

The particle beam therapy device of the present invention may include a degrader provided on an upstream side of the deflection magnetic field and that causes energy of the cation beam to be reduced. In such a degrader, when the energy of the cation beam is reduced, the other species of the beam having a nuclide different from that of the cation beam is likely to be generated, and the other species of the beam is reduced by the deflection magnetic field and the passage selection unit as described above.

The degrader may be provided in the gantry, and the deflection magnetic field and the passage selection unit may be provided in the gantry. Since the degrader, the deflection magnetic field, and the passage selection unit are provided in the gantry, a beam transport system on the upstream side of the gantry can be shortened, and the size of the particle beam therapy device can be reduced.

In this particle beam therapy device, an energy-fixed cation beam is exited from the cyclotron due to the nature of the cyclotron. By reducing the energy of the cation beam with a degrader, the cation beam can be adjusted to the energy suitable for treatment. In the degrader, the other species of the beam having a different nuclide is generated from the cation beam, and the mixed beam in which the cation beam and the other species of the beam are mixed is transmitted to the downstream side of the degrader. The mixed beam is deflected by the bending electromagnet, and the trajectory of each of the beams included in the mixed beam is different depending on the momentum per unit charge on the downstream side of the bending electromagnet.

Thereafter, the passage selection unit passes through the beam included in the mixed beam at the position of the trajectory of the cation beam in the mixed beam. Here, since the cation beam exited from the cyclotron exhibits a biased energy distribution in a single nuclide due to the nature of the cyclotron, the momentum per unit charge is relatively biased in the cation beam after the energy is reduced by the degrader. Therefore, by aiming at the position of the trajectory corresponding to the momentum per unit charge of the cation beam, it is possible to set the passage selection unit to pass through most of the cation beam included in the mixed beam. On the other hand, since the other species of the beam is generated when the energy of the cation beam is reduced in the degrader, the variation in the momentum per unit charge is larger than that of the cation beam derived from the cyclotron. In addition, as described above, since the region where the momentum per unit charge of the cation beam after the energy is reduced is biased is considered to be relatively narrow, the range of momentum per unit charge of the beam to be passed through by the passage selection unit can be made relatively narrow. Therefore, even when the beam having the momentum per unit charge equivalent to that of the cation beam among the other species of the beam passes through the passage selection unit, the amount of beam passes is suppressed to be small and most of the other species of the beams are shielded by the passage selection unit. As a result, the other species of the beam is reduced from the cation beam irradiated to the patient on the downstream side of the passage selection unit.

According to the present invention, it is possible to provide a particle beam therapy device that reduces an unnecessary particle beam irradiated to the patient.

Hereinafter, a preferred embodiment of a particle beam therapy device according to the present invention will be described with reference to the drawings. In the description of the drawings, the same elements are designated by the same reference numerals, and redundant descriptions will be omitted. A particle beam therapy device 1 of the present embodiment is applied to, for example, cancer treatment, and a charged particle beam therapy device that treats a tumor in a patient's body by irradiating a helium ion beam ($\alpha$-ray), which is a type of cation beam.

FIG. 1 is a disposition view of the particle beam therapy device 1 in a plan view. As illustrated in FIG. 1, the particle beam therapy device 1 is provided with an accelerator 3 that exits a helium ion beam, an irradiator 9 that irradiates a patient 7 on a treatment table 5 with a helium ion beam, and a transporter 11 that transports the helium ion beam exited from the accelerator 3 to the irradiator 9. The particle beam therapy device 1 is installed in, for example, a one-story building 13.

The accelerator 3 accelerates a helium nucleus (a particle) and exits the helium ion beam. In the present embodiment, the accelerator 3 is a cyclotron (for example, a superconducting cyclotron). The irradiator 9 is mounted on a rotatable gantry 15. The gantry 15 is provided so as to surround the treatment table 5, and is rotatable around a predetermined rotation axis H in the vicinity of the treatment table 5 in the building 13. The irradiator 9 can rotate and move around the patient 7 on the treatment table 5 as the gantry 15 rotates, and can irradiate the patient 7 with a helium ion beam from various directions. In addition, the irradiator 9 includes, for example, a scanning electromagnet or a multi-leaf collimator (not illustrated), and irradiates the tumor of the patient 7 while scanning the helium ion beam.

Subsequently, the transporter 11 will be described. Hereinafter, the upstream and downstream directions of the helium ion beam in the transporter 11 are defined as a Z direction, one direction perpendicular to the Z direction is defined as an X direction, and the directions perpendicular to both the Z direction and the X direction are defined as a Y direction. In the state illustrated in FIG. 1, in each part of the transporter 11, a direction perpendicular to the paper surface of FIG. 1 is defined as a Y direction. The transporter 11 is provided with a beam duct 17, and a large number of bending electromagnets 21 and quadrupole electromagnets 23 disposed along the beam duct 17. For example, the bending electromagnet 21 is a normal conduction electromagnet. The transporter 11 includes an external path 11A that transports the helium ion beam from the accelerator 3 to an inlet 15a of the gantry 15, and an internal path 11B that is provided in the gantry 15 and transports the helium ion beam from the inlet 15a of the gantry 15 to the irradiator 9. The external path 11A is fixed to the building 13, and the internal path 11B rotates around the rotation axis H as a whole with the rotation of the gantry 15.

The beam duct 17 is a vacuum duct through which the helium ion beam passes. The bending electromagnet 21 deflects the traveling direction of the helium ion beam in the X direction by forming a deflection magnetic field in the Y direction in the beam duct 17. By providing such a bending electromagnet 21, the transport path of the helium ion beam can be curved at a desired position in the building 13, and the transporter 11 can be formed into a desired shape. The quadrupole electromagnet 23 includes an electromagnet that converges the helium ion beam in the X direction and an electromagnet that converges the helium ion beam in the Y direction. The helium ion beam is focused by the quadrupole electromagnet 23 during transportation by the transporter 11, and the beam shape is adjusted.

The accelerator 3 of the particle beam therapy device 1 exits a helium ion beam having a fixed energy due to the nature of the cyclotron, and cannot adjust the energy of the helium ion beam. Therefore, the particle beam therapy device 1 is provided with a degrader 27 provided in the beam duct 17 on the external path 11A. The degrader 27 is provided at a portion of the external path 11A that extends linearly to the downstream side from the accelerator 3. That is, the degrader 27 is disposed on the further upstream side than the bending electromagnet 21 disposed on the most upstream side of the transporter 11.

The degrader 27 has, for example, a plate-shaped damping member made of a predetermined material (for example, graphite or beryllium). In the degrader 27, the energy of the helium ion beam is reduced as the helium ion beam passes through the damping member. In this manner, by reducing the energy of the helium ion beam by the degrader 27, the energy of the helium ion beam transmitted to the irradiator 9 is adjusted to be suitable for the treatment of the patient 7. A collimator (not illustrated) for cutting a beam deviating from the aperture of the transporter 11 is installed on an immediate downstream side of the damping member of the degrader 27.

In the degrader 27, a part of the helium nuclei decays when the helium ion beam passes through the damping member, so that another nuclide of a particle beam such as deuterium, tritium, neutron, helium 3, and hydrogen is generated, and a deuterium ion beam, a tritium ion beam, a neutron ion beam, a helium 3 ion beam, a hydrogen ion beam, and the like are generated. A beam (hereinafter, referred to as a "mixed beam") in which a helium ion beam used for treatment and the other nuclide of the beam as described above (hereinafter, referred to as "other species of the beam") unnecessary for treatment are mixed is transported to the downstream side from the degrader 27.

Figure 2A:
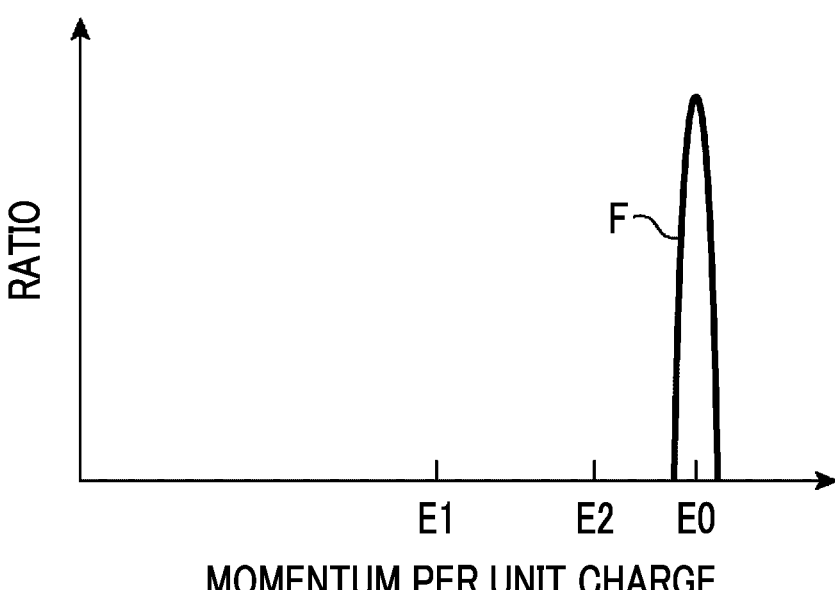
FIG. 2A is a graph schematically illustrating a distribution of momentum per unit charge of a helium ion beam exited from an accelerator.
Figure 2B:
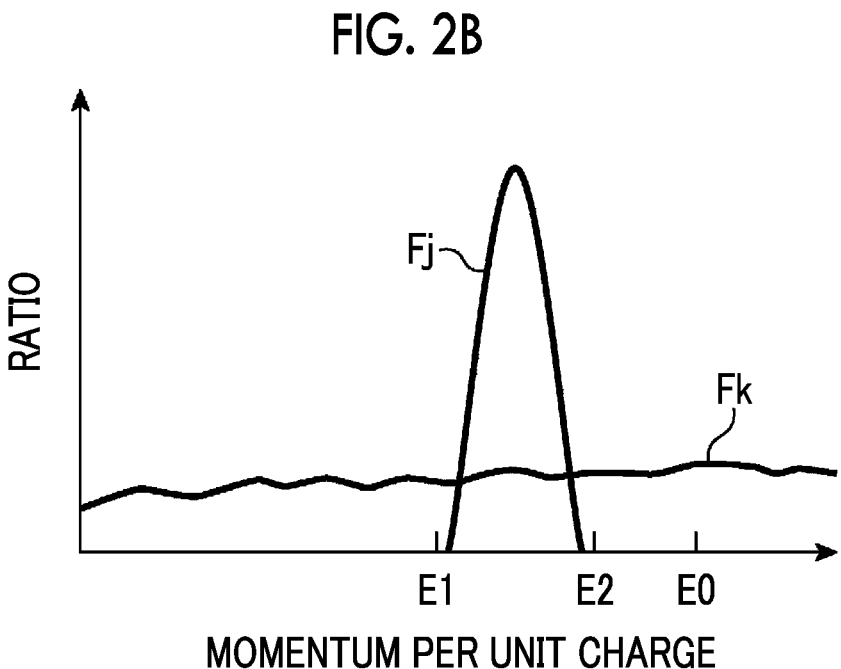
FIG. 2B is a graph schematically illustrating a distribution of the momentum per unit charge of a reduced helium ion beam and a distribution of the momentum per unit charge of other species of a beam superimposed.

FIG. 2A is a graph schematically illustrating a distribution F of the momentum per unit charge of the helium ion beam exited from the accelerator 3. FIG. 2B is a graph schematically illustrating a distribution Fj of the momentum per unit charge of a helium ion beam passed through the degrader 27 and a distribution Fk of the momentum per unit charge of the other species of the beam generated by the degrader 27 superimposed.

The distribution of the momentum per unit charge of the helium ion beam exited from the accelerator 3 illustrates a sharp peak at E0 due to the nature of the cyclotron such that a single nuclide of a particle beam biased to a predetermined energy is exited. In this manner, the momentum per unit charge of the helium ion beam exited from the accelerator 3 is E0, whereas the momentum per unit charge of the helium ion beam corresponding to the energy suitable for the treatment of the patient 7 is E1 to E2 (here, E2<E0).

As illustrated in FIGS. 2A and 2B, the momentum per unit charge of the helium ion beam is reduced from E0 to E1 to E2 by passing through the degrader 27. As illustrated in FIG. 2B, the distribution of the momentum per unit charge of the helium ion beam after the reduction illustrates a slower peak than before the reduction, but is still distributed in a relatively narrow range of E1 to E2. On the other hand, as illustrated in FIG. 2B, the momentum per unit charge of the other species of the beam generated by the degrader 27 significantly varies and is distributed over a wide range across E1 to E2.

Here, in the particle beam irradiated to the patient 7, the range in the body of the patient 7 changes depending on the mass number, the charge state, and the velocity of the particles. That is, the range of the heavily charged particle is approximately proportional to $(A/Q2) \times v4$ (here, A is a mass number, Q is a charge state, and v is a velocity).

Therefore, when the patient 7 is irradiated with the other species of the beam having a mass number, a charge state, and a velocity different from those of the helium nucleus, there is a high possibility that a portion on the front side or the rear side with respect to the tumor is unnecessarily damaged.

Therefore, it is desirable that the other species of the beam generated by the degrader 27 as described above is removed as much as possible before reaching the patient 7.

Therefore, as illustrated in FIG. 1, the particle beam therapy device 1 is provided with a beam sorting unit 31 provided in the transporter 11 on the downstream side of the degrader 27. The beam sorting unit 31 selectively shields the other species of the beam among the mixed beams transported to the downstream side from the degrader 27, and selectively passes through the helium ion beam used for the treatment. The description of "selectively passing through" the helium ion beam does not mean that any beams other than the helium ion beam are not caused to pass through, but means to make the helium ion beam relatively easy to pass through, and make the other beams relatively difficult to pass through. Similarly, the description of "selectively shielding" the other species of the beam does not mean that any beams other than the other species of the beam are not shielded, but means to make the other species of the beam relatively easy to shield, and make the other beams relatively difficult to shield.

Specifically, the beam sorting unit 31 includes one bending electromagnet 21A disposed on the downstream side of the degrader 27 of the bending electromagnets 21 of the transporter 11, and a passage selection unit 33 disposed on the further downstream side of the bending electromagnet 21A. The bending electromagnet 21A constituting the beam sorting unit 31 is a bending electromagnet 21 through which the mixed beam generated by the degrader 27 first passes. That is, the quadrupole electromagnet 23 may be disposed between the degrader 27 and the bending electromagnet 21A, but the other bending electromagnet 21 is not disposed.

The passage selection unit 33 is, for example, a member that opens a part of the cross section of the beam duct 17 in the X direction and causes the beam to pass through the opening portion. The passage selection unit 33 is disposed on the upstream side of the bending electromagnet 21 disposed on the downstream side next to the bending electromagnet 21A. That is, there is a case where the quadrupole electromagnet 23 is disposed between the bending electromagnet 21A and the passage selection unit 33 constituting the beam sorting unit 31, but the other bending electromagnet 21 is not disposed. In the example of FIG. 1, neither the quadrupole electromagnet 23 nor the other bending electromagnet 21 is disposed between the bending electromagnet 21A and the passage selection unit 33.

Figure 3A:
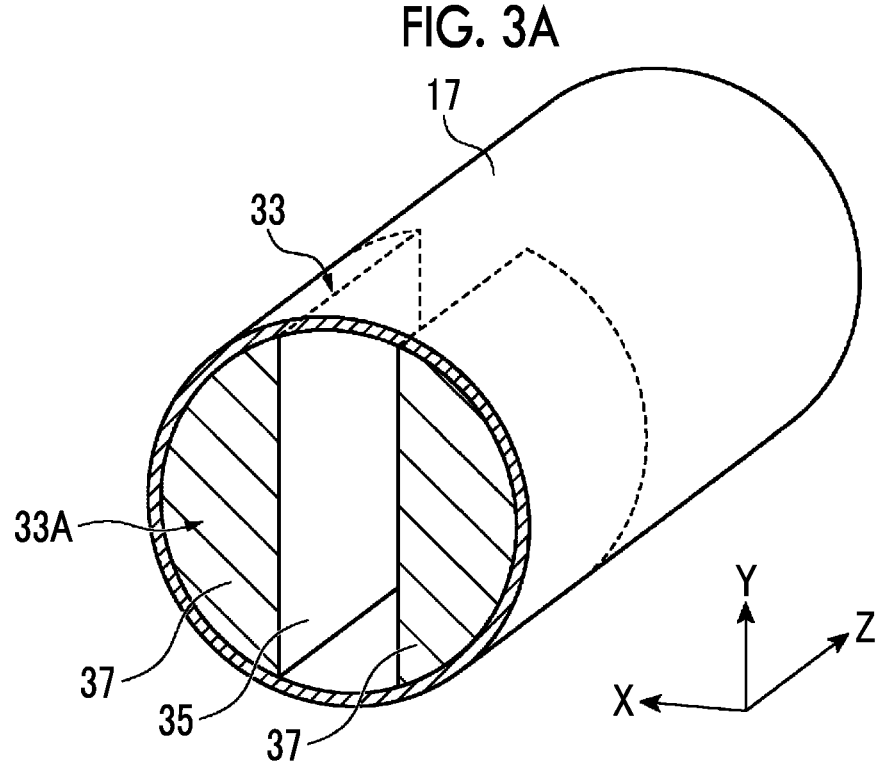
FIGS. 3A and 3B are perspective views schematically illustrating the vicinity of a passage selection unit of each example with a part cut away.
Figure 3B:
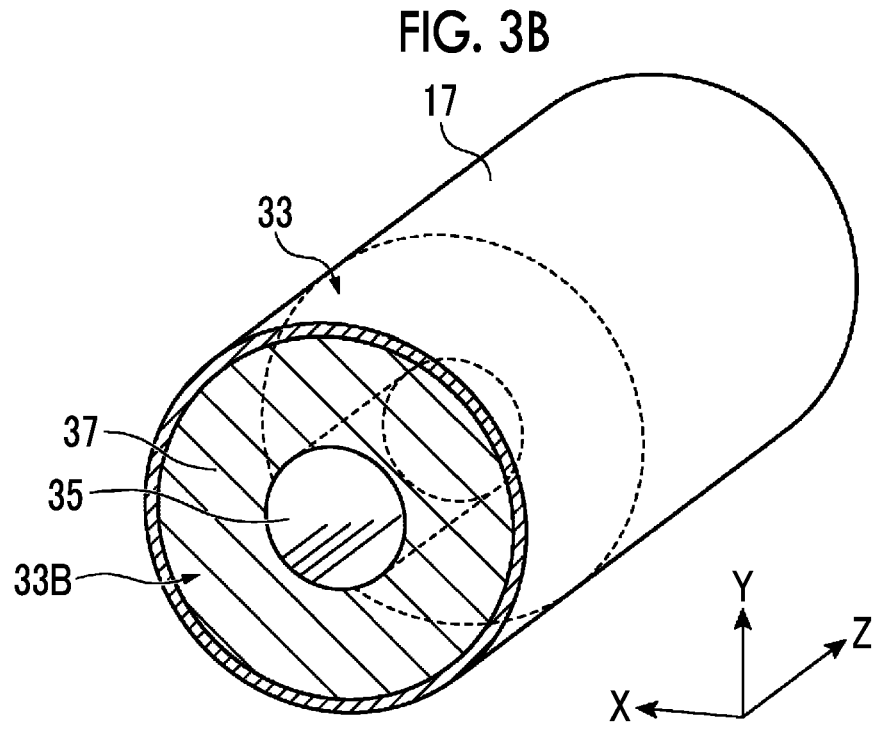

FIGS. 3A and 3B are perspective views schematically illustrating the vicinity of the passage selection unit 33 with a part cut away. As the passage selection unit 33, for example, a slit member 33A illustrated in FIG. 3A may be adopted. In the slit member 33A, a slit that is open to cause the beam to pass through is formed as a beam passage unit 35 in a partial range in the X direction of the cross section of the beam duct 17. A beam shielding unit 37 that causes the beam to collide and shields the beam is formed at a position other than the beam passage unit 35.

Figure 4:
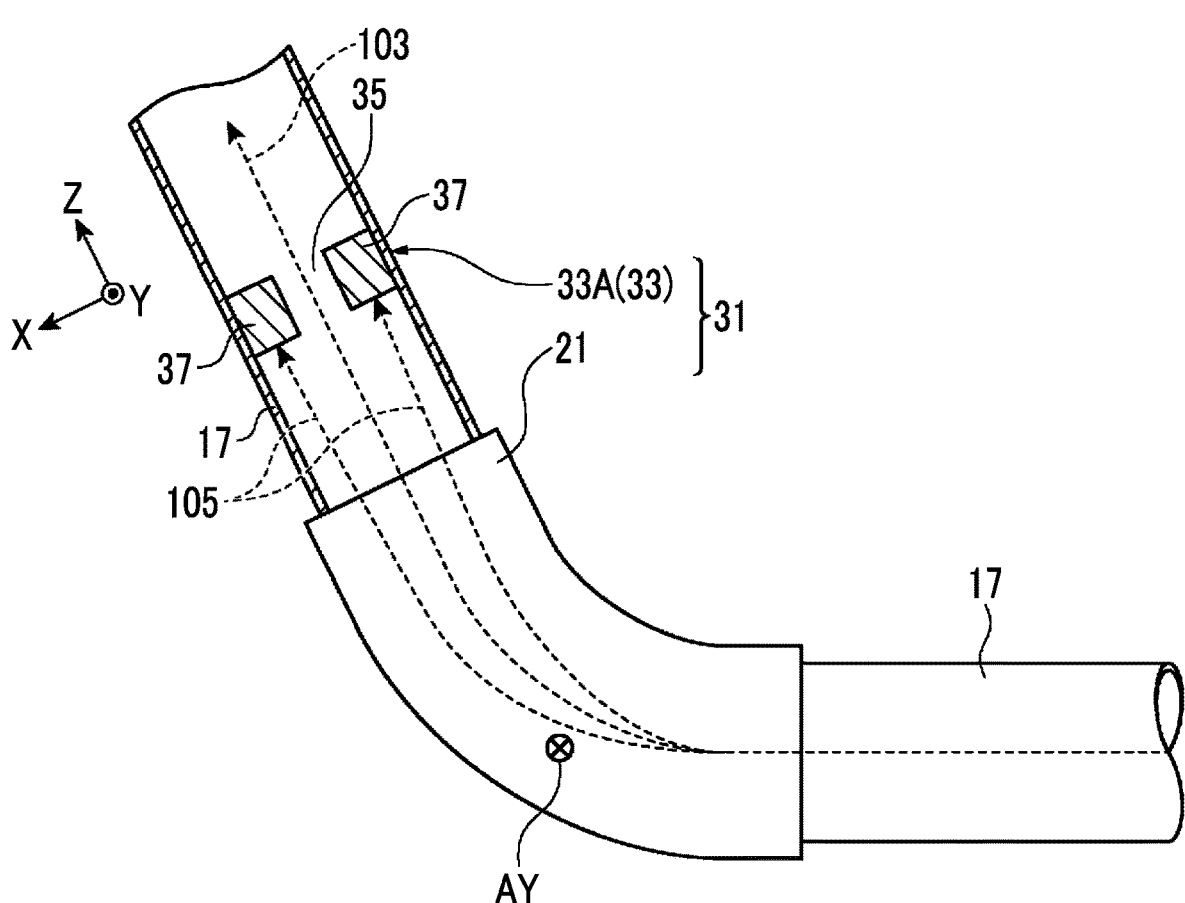
FIG. 4 is an enlarged view illustrating the vicinity of a beam sorting unit.

FIG. 4 is an enlarged view illustrating the vicinity of the beam sorting unit 31. In the beam sorting unit 31, as illustrated in FIG. 4, the traveling direction of the mixed beam 101 is curved by the deflection magnetic field AY in the Y direction formed in the beam duct 17 by the bending electromagnet 21A. The radius of curvature of the curve of each beam included in the mixed beam 101 depends on the momentum per unit charge of the beam, the higher the momentum per unit charge of the beam, the larger the radius of curvature, and the lower the momentum per unit charge of the beam, the smaller the radius of curvature. As a result, the trajectory of each beam included in the mixed beam 101 differs for each momentum per unit charge, and the passing position of each beam in the X direction differs for each momentum per unit charge at the position of the slit member 33A. Among the mixed beam 101, only the beam having the momentum per unit charge of E1 to E2 passes through the beam passage unit 35 in, for example, a trajectory 103 and is transported to the downstream side. Among the mixed beam 101, the beam having the momentum per unit charge less than E1 or more than E2 is transported in, for example, a trajectory 105, collides with the beam shielding unit 37, and is shielded.

As a result, most of the helium ion beams included in the mixed beam pass through the passage selection unit 33, and most of the other species of the beams are shielded by the passage selection unit 33 except those having the momentum per unit charge of E1 to E2. That is, the passage selection unit 33 selectively passes through the helium ion beam used for the treatment among the mixed beams, and the beam sorting unit 31 selectively passes through the helium ion beam used for the treatment among the mixed beams.

As the passage selection unit 33, the collimator 33B, an example of which is illustrated in FIG. 3B, may be adopted instead of the slit member 33A. The beam passage unit 35 in the collimator 33B is formed of an opening provided near the center of the cross section of the beam duct 17 instead of the slit described above. The opening has a circular shape in the example of FIG. 3B, but may be a quadrangular shape. The passage selection unit 33 that employs such a collimator 33B also selectively passes through the helium ion beam of the mixed beam.

Subsequently, the action and effect of the particle beam therapy device 1 will be described. In the particle beam therapy device 1, an energy-fixed helium ion beam is exited from the accelerator 3 due to the nature of the cyclotron. By reducing the energy of the helium ion beam with the degrader 27, the helium ion beam can be adjusted to an energy suitable for the treatment. Thereafter, when the mixed beam transported from the degrader 27 to the downstream side is deflected by the bending electromagnet 21A and the trajectory is curved, since the curvature of the curve differs depending on the momentum per unit charge of the beam, the trajectory of each beam included in the mixed beam differs in the X direction according to the momentum per unit charge on the downstream side of the bending electromagnet 21A.

Thereafter, the passage selection unit 33 passes through the beam included in the mixed beam at the position of the trajectory of the helium ion beam in the mixed beam. Here, the helium ion beam exited from the accelerator 3 exhibits the distribution of the momentum per unit charge biased to E0 due to the nature of the cyclotron. Therefore, the helium ion beam after the energy is lowered by the degrader 27 also exhibits a distribution of momentum per unit charge relatively biased toward E1 to E2. Therefore, by providing the beam passage unit 35 aiming at the position of the trajectory corresponding to the range E1 to E2 of the momentum per unit charge of the helium ion beam (the position of the trajectory 103 in FIG. 4), the passage selection unit 33 can be set to pass through most of the helium ion beam contained in the mixed beam.

On the other hand, since the other species of the beam is accidentally generated by the collision between the helium ion beam and the degrader 27, the variation in the momentum per unit charge is larger than that of the helium ion beam derived from the cyclotron. In addition, as described above, since the ranges E1 to E2 in which the momentum per unit charge of the helium ion beam is biased are relatively narrow, the beam passage unit 35 can be relatively narrowed. Therefore, even when the beams having the momentum per unit charge of E1 to E2 equivalent to that of the helium ion beam among the other species of the beams pass through the beam passage unit 35, the amount of beam is suppressed to be small and most of the other species of the beams are shielded by the beam shielding unit 37. As a result, the other species of the beam is reduced from the helium ion beam transmitted to the downstream side of the passage selection unit 33. Therefore, the other species of the beam with which the patient 7 is irradiated is reduced, and unnecessary damage to a portion other than the tumor is reduced. In addition, radio-activation and malfunction of each device of the transporter 11 caused by the other species of the beam are also reduced.

Another Embodiment

Figure 5:
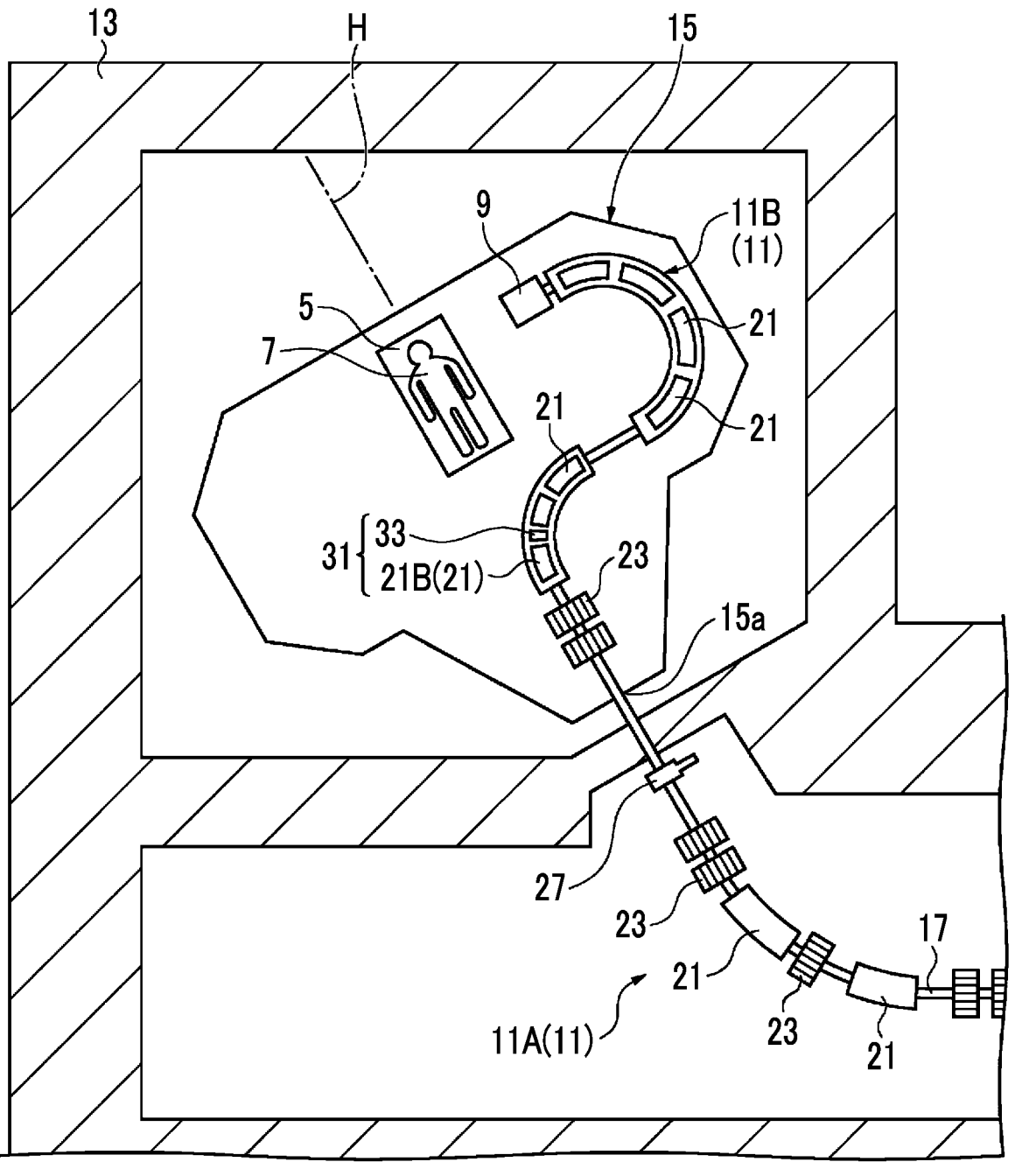
FIG. 5 is an enlarged view illustrating a main part in a plan view of a particle beam therapy device according to another embodiment.

In the present embodiment, the same or equivalent components as those in the one embodiment are designated by the same reference numerals, and redundant descriptions will be omitted. In the particle beam therapy device of the present embodiment, as illustrated in FIG. 5, the degrader 27 is provided on the immediate upstream side of the inlet 15a of the gantry 15. The beam sorting unit 31 is constructed in the internal path 11B in the gantry 15. The beam sorting unit 31 includes one bending electromagnet 21B in the gantry 15, and a passage selection unit 33 disposed on the downstream side of the bending electromagnet 21B. In this manner, in a configuration in which the beam sorting unit 31 is provided in the gantry 15, it is not always necessary to provide the bending electromagnet 21 in the external path 11A extending from the accelerator 3 to the inlet 15a of the gantry 15. Therefore, the external path 11A can be made a straight line, and the external path 11A can be shortened. By shortening the external path 11A, it is possible to reduce the size of the particle beam therapy device as a whole.

Further Embodiment

Figure 6:
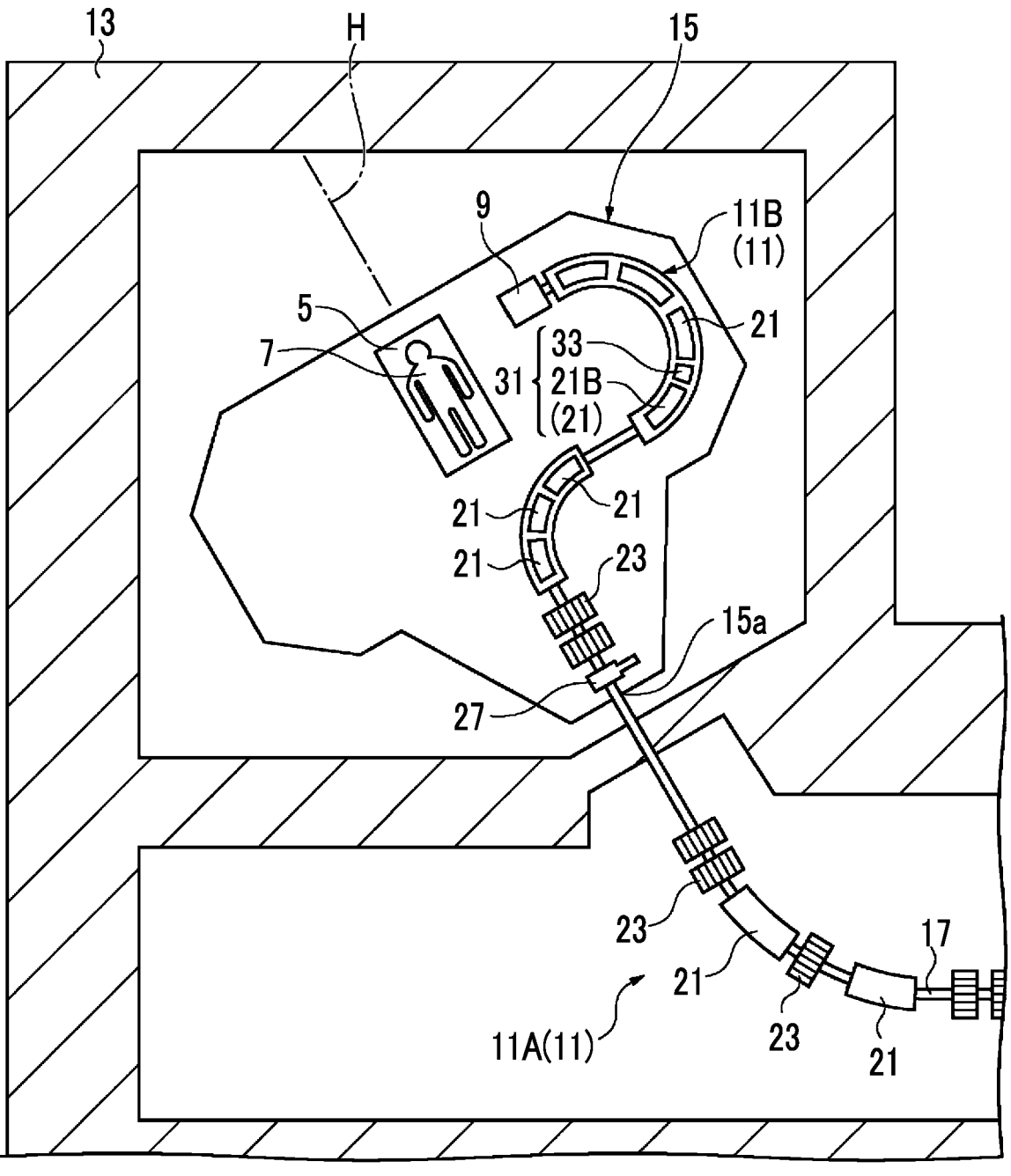
FIG. 6 is an enlarged view illustrating a main part in a plan view of a particle beam therapy device according to further embodiment.

In the present embodiment, the same or equivalent components as those in the one or another embodiment are designated by the same reference numerals, and redundant descriptions will be omitted. In the particle beam therapy device of the present embodiment, as illustrated in FIG. 6, the degrader 27 is provided in the internal path 11B in the gantry 15. The degrader 27 is provided on the immediate downstream side of the inlet 15a of the gantry 15. The beam sorting unit 31 is constructed on the downstream side of the degrader 27 in the internal path 11B in the gantry 15. The beam sorting unit 31 includes one bending electromagnet 21B in the gantry 15, and a passage selection unit 33 disposed on the downstream side of the bending electromagnet 21B. In this manner, in a configuration in which the degrader 27 is provided in the gantry 15 as compared with the other embodiment, the external path 11A can be further shortened, and it is possible to further reduce the size of the particle beam therapy device as a whole.

The present invention can be performed in various embodiments with various modifications and improvements based on the knowledge of those skilled in the art, including each embodiment described above. In addition, it is also possible to configure a modification example by using the technical matters described in the embodiment described above. Configurations such as each embodiment may be used in combination as appropriate. For example, in the beam sorting unit 31, the passage selection unit 33 including the slit member 33A or the collimator 33B may be installed in the deflection magnetic field AY formed by the bending electromagnet 21A instead of the downstream side of the bending electromagnet 21A.

In addition, the present invention is not limited to the helium ion beam therapy device, and can be applied to various particle beam therapy devices. In particular, the present invention is suitably applicable in a case where particles of a particle beam used for treatment can decay when passing through the degrader 27 to generate the other species of the beam. Here, considering a proton beam therapy device in which a proton beam is used for treatment, the protons cannot be further smaller particles when the energy is reduced by the degrader 27, and the other species of the beam cannot be generated. Therefore, the present invention is suitably applicable to a particle beam therapy device that uses a particle beam other than a proton beam for treatment. Examples of such a particle beam include a carbon ion beam (carbon beam) in addition to the helium ion beam. In a case where the carbon ion beam is passed through the degrader 27, the other species of the beams such as a hydrogen ion beam, a deuterium ion beam, and a helium ion beam are generated, but these other species of the beams irradiated to the patient 7 can be reduced by the beam sorting unit 31.

It should be understood that the invention is not limited to the above-described embodiment, but may be modified into various forms on the basis of the spirit of the invention. Additionally, the modifications are included in the scope of the invention.

What is claimed is:

1. A particle beam therapy device that irradiates a patient with a cation beam to perform treatment, the device comprising:
   an accelerator that emits the cation beam;
   an irradiator that irradiates the patient with the cation beam; and
   a transporter that transports the cation beam emitted from the accelerator to the irradiator and includes
      a bending electromagnet configured to generate a deflection magnetic field, and
      a passage that includes
         an opening configured to selectively allow the cation beam in a mixed beam to pass through the deflection magnetic field, in a case where other species of a beam is generated from the cation beam, the mixed beam being a beam in which the cation beam and the other species of the beam having a nuclide different from that of the cation beam are mixed, and a shield configured to shield the other species of the beam having a nuclide different from that of the cation beam in the mixed beam.

2. The particle beam therapy device according to claim 1, wherein
   the passage allows a beam having the same momentum per unit charge as momentum per unit charge of the cation beam in the mixed beam passed through the deflection magnetic field to pass through, and shields a beam having momentum per unit charge different from the momentum per unit charge of the cation beam in the mixed beam.

3. The particle beam therapy device according to claim 1, wherein
   the deflection magnetic field causes a trajectory of a beam included in the mixed beam to be different depending on the momentum per unit charge on an upstream side of the passage, and
   the passage causes the beam included in the mixed beam to pass through at a position of a trajectory corresponding to the momentum per unit charge of the cation beam included in the mixed beam, and shields the beam included in the mixed beam at a position other than the position of the trajectory corresponding to the momentum per unit charge of the cation beam included in the mixed beam.

4. The particle beam therapy device according to claim 1, wherein
   the cation beam is a helium ion beam, and the other species of the beam includes a deuterium ion beam.

5. The particle beam therapy device according to claim 1, further comprising:
   a degrader that is provided on an upstream side of the deflection magnetic field and causes energy of the cation beam to be reduced.

6. The particle beam therapy device according to claim 5, wherein
   the degrader is provided in a gantry, and the deflection magnetic field and the passage are provided in the gantry.

7. The particle beam therapy device according to claim 6, wherein
   the degrader is disposed on a further upstream side from the deflection magnetic field.

8. The particle beam therapy device according to claim 1, wherein
   the cation beam is a helium ion beam.

9. The particle beam therapy device according to claim 8, wherein
   the accelerator is a cyclotron that accelerates a helium nucleus and emits the helium ion beam.

10. The particle beam therapy device according to claim 8, wherein
   the transporter includes a beam duct, and a plurality of bending electromagnets and a plurality of quadrupole electromagnets disposed along the beam duct.

11. The particle beam therapy device according to claim 8, wherein
   the transporter includes an external path for transporting the helium ion beam from the accelerator to an inlet of a gantry, and an internal path provided in the gantry for transporting the helium ion beam from the inlet of the gantry to the irradiator.

12. The particle beam therapy device according to claim 11, wherein
   the internal path of the transporter rotates around a rotation axis as the gantry rotates.

13. A particle beam therapy device that irradiates a patient with a cation beam to perform treatment, the device comprising:

a cyclotron that emits the cation beam;

a degrader that is provided on a downstream side of the cyclotron, reduces energy of the cation beam, and generates other species of a beam having a nuclide different from that of the cation beam from the cation beam when the energy is reduced;

a bending electromagnet that is provided on a downstream side of the degrader and is configured to generate a deflection magnetic field and deflect a mixed beam in which the cation beam and the other species of the beam are mixed to cause a trajectory of a beam included in the mixed beam to be different depending on momentum per unit charge; and a passage provided on a downstream side of the bending electromagnet and includes an opening configured to selectively allow the beam included in the mixed beam to pass through at a position of a trajectory of the cation beam in the mixed beam, and a shield configured to shield the beam included in the mixed beam at a position other than the position of the trajectory of the cation beam in the mixed beam.

* * * * *